(12) United States Patent
Bernhardt

(10) Patent No.: US 7,489,762 B2
(45) Date of Patent: Feb. 10, 2009

(54) METHOD FOR RECORDING PROJECTION IMAGES

(75) Inventor: Philipp Bernhardt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/728,902

(22) Filed: Mar. 27, 2007

(65) Prior Publication Data

US 2007/0242795 A1    Oct. 18, 2007

(30) Foreign Application Priority Data

Mar. 29, 2006   (DE) .................. 10 2006 014 624

(51) Int. Cl.
*H05G 1/64*    (2006.01)
(52) U.S. Cl. .................. 378/98.9; 378/62; 378/116
(58) Field of Classification Search ............. 378/98.8, 378/98.9, 98.11, 98.12, 62, 116
See application file for complete search history.

(56) References Cited

U.S. PATENT DOCUMENTS

| 5,253,282 | A  | 10/1993 | Pelc |
| 6,393,097 | B1 | 5/2002  | Aufrichtig et al. |

FOREIGN PATENT DOCUMENTS

| DE | 42 30 974 C1  | 12/1993 |
| DE | 693 19 403 T2 | 5/1994 |
| DE | 101 95 715 T5 | 11/2004 |

OTHER PUBLICATIONS

Richard J. Warp and James T. Dobbins III, "Quantitative evaluation of noise reduction strategies in dual-energy imaging", Med. Phys, Feb. 2003, pp. 190-198, vol. 30, No. 2.

*Primary Examiner*—Jurie Yun

(57) ABSTRACT

In a method for performing recordings for dual absorptiometry, a high-energy radiation pulse is performed before a low-energy radiation pulse. Furthermore the high-energy radiation pulse is arranged at the end of an assigned radiation window of the detector. This temporal sequence of a high-energy radiation pulse and a low-energy radiation pulse allows the total time for performing the recordings for dual absorptiometry to be minimized.

16 Claims, 1 Drawing Sheet

METHOD FOR RECORDING PROJECTION IMAGES

CROSS REFERENCE TO RELATED APPLICATIONS

This application claims priority of German application No. 10 2006 014 624.7 filed Mar. 29, 2006, which is incorporated by reference herein in its entirety.

FIELD OF THE INVENTION

The invention relates to a method for recording projection images of an object under examination, with which method radiation pulses are emitted by a radiation source during radiation windows of a radiation detector in a high-energy range and a low-energy range and are recorded by the radiation detector.

BACKGROUND OF THE INVENTION

A method of said type is known from DE 101 95 715 T5. According to the known method first an x-ray pulse in the low-energy range and then a further x-ray pulse in the high-energy range are emitted by the x-ray source. The radiation emitted by the x-ray source in the high-energy range and in the low-energy range penetrates an object under examination and is recorded by an x-ray detector, which in turn produces projection images of the object under examination. From the projection images recorded in the high-energy and low-energy range a combined image can then be produced by an evaluation unit connected downstream of the x-ray detector.

Because the absorption behavior of the irradiated material of the object under examination differs depending on the energy of the irradiating x-radiation, combined images can be produced by combining the projection images, said combined images reproducing the structural distribution of a specific material within the object under examination. For example structural distributions of two different materials having different absorption characteristics can be resolved when two projection images are recorded in different energy ranges.

A fundamental problem with such methods is that the temporal interval between the radiation pulse in the low-energy range and the radiation pulse in the high-energy range must not be allowed to become too long, because motion artifacts will otherwise occur in the combined image.

A further problem concerns semiconductor x-ray detectors, which must always be operated in a particular mode. The mode is defined by the number of detector elements read out, the read-out frequency and the duration of the x-ray window. X-ray window means the period of time during which the semiconductor x-ray detector can record x-radiation. A change of the mode in which the semiconductor x-ray detector is operated frequently leads to switching artifacts, which are also known as modeswitch artifacts. Current offset images are also necessary for every mode of the x-ray detector, in order to be able to perform offset adjustments to the recorded projection images. As the number of modes in which the detector is operated increases, the number of offset images required for the offset adjustment also increases. Thus the effort required for the offset adjustment becomes greater.

Since motion artifacts are furthermore to be expected in medical procedures, in the known method the offset images are recorded in a temporal interval from the projection images. Switching modes between recording in the high-energy range and recording in the low-energy range is also not possible. The duration of the x-ray window for recording in the high-energy range and recording in the low-energy range is thus equally long.

However the duration of the radiation pulse in the high-energy range is set to be smaller than the duration of the radiation pulse in the low-energy range, because the effective cross-section of the x-ray quanta in terms of material decreases as the energy of the x-ray quanta increases. With constant exposure time the x-ray detector receives a higher detector dosage from the radiation pulse in the high-energy range than from the radiation pulse in the low-energy range. For this reason in the known method the exposure time for the radiation pulse in the high-energy range is set lower than the exposure time for the radiation pulse in the low-energy range.

In order to obtain an adequate detector dosage during the radiation pulse in the low-energy range the tube current must be set high, since the exposure time must not be allowed to become so long as to unnecessarily increase the danger of motion artifacts.

In order to reduce the tube current in the transition from the x-ray source settings for the radiation pulse in the high-energy range to the settings for the radiation pulse in the low-energy range the incandescent filament of the cathode of the x-ray source must be cooled down. Since time is required for this, the radiation pulse in the high-energy range cannot immediately follow the radiation pulse in the low-energy range. Time is also required for reading out data from the x-ray detector. The x-ray detector readout takes place after the x-ray window has closed, and thus for this reason too it is not possible for the radiation pulse in the high-energy range to follow the radiation pulse in the low-energy range immediately.

Owing to this delay further motion artifacts can occur.

SUMMARY OF THE INVENTION

Proceeding from this prior art, the object underlying the invention is therefore to disclose a method for recording projection images in different energy ranges, avoiding motion artifacts where possible.

Said object is achieved by means of a method having the features of the independent claim. Advantageous embodiments and developments are indicated in the dependent claims.

According to the method, the recording in the high-energy range takes place before the recording in the low-energy range, and consequently the time between the two recordings can be reduced, because as a rule the photon current density can be increased more quickly than it can be decreased. Photon current density is taken here to mean the number of photons that strike a unit of area of the radiation detector per unit of time. In order to keep the interval between the radiation pulse in the high-energy range and the radiation pulse in the low-energy range as low as possible, the radiation pulse in the high-energy range is performed at the end of the assigned radiation window. The temporal interval between the radiation pulse in the high-energy range and the radiation pulse in the low-energy range can be minimized through the temporal sequence of the radiation pulse in the high-energy range and the radiation pulse in the low-energy range, thus suppressing motion artifacts where possible.

The radiation windows that are assigned to each radiation pulse in the high-energy range and in the low-energy range are preferably of the same duration. Artifacts resulting from switching modes are thus avoided.

The duration of the radiation pulse in the high-energy range is also preferably shorter than the duration of the radiation pulse in the low-energy range in order to minimize the patient's exposure to radiation.

In a preferred embodiment an x-ray source is used as a radiation source and an x-ray detector is used as a detector, comprising an x-ray tube with a heated cathode. In the case of an x-ray tube with heated cathode in particular, the photon current density can be increased more rapidly by heating than it can be reduced by cooling.

BRIEF DESCRIPTION OF THE DRAWINGS

Further advantages and characteristics of the invention will emerge from the following description in which exemplary embodiments of the invention are explained in detail with the aid of the attached drawing, in which.

DETAILED DESCRIPTION OF THE INVENTION

Figure 1:
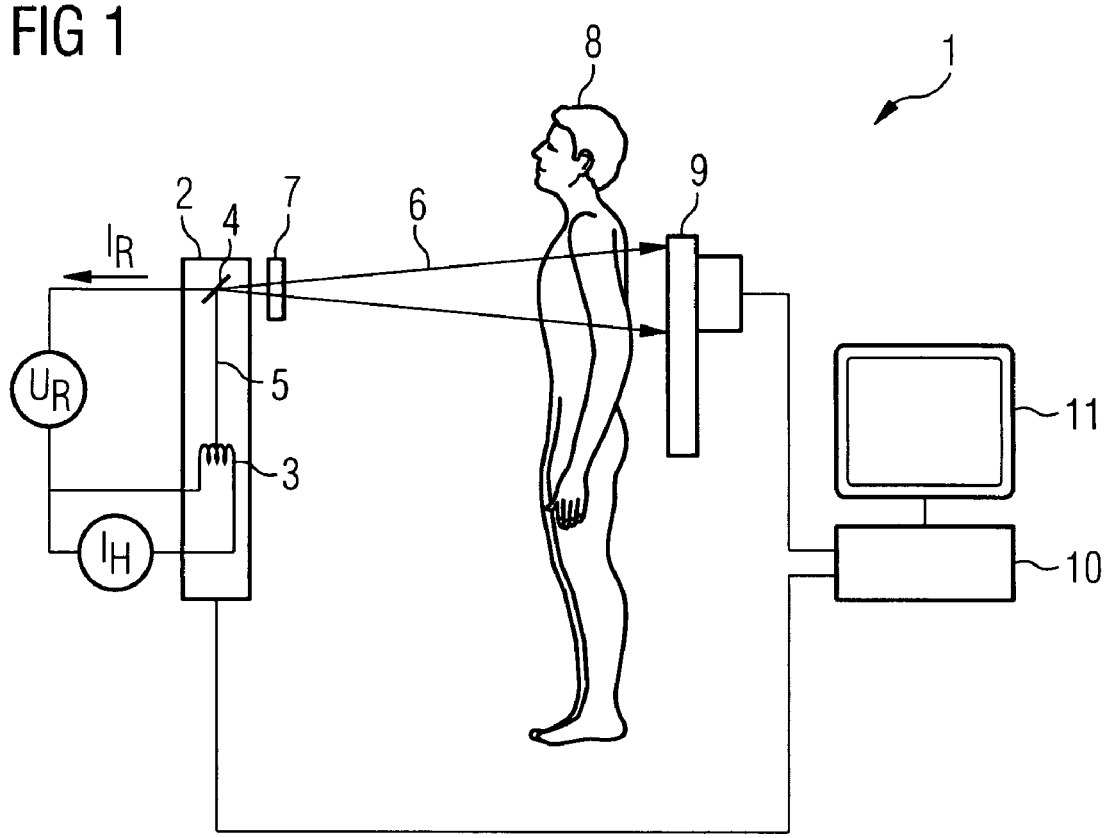
FIG. 1 shows a schematic representation of an x-ray system with which x-ray recordings for dual x-ray absorptiometry can be produced.

FIG. 1 shows an x-ray system 1 with which x-ray recordings for dual x-ray absorptiometry can be performed. The x-ray system 1 comprises an x-ray tube 2 having a cathode 3 in the form of an incandescent filament. The incandescent filament 3 can be heated with the aid of a heater current $I_H$. The cathode 3 emits electrons that are accelerated in the direction of an anode 4 with the aid of a tube voltage $U_R$. That produces an electron beam 5 that strikes the anode 4 in a focused spot. The electrons retarded in the anode 4 produce x-radiation 6, which first passes through a preliminary filter 7 to suppress the low-energy component. The preliminary filters 7 are as a rule copper plates that can be interposed having different thickness into the beam path of the x-radiation 6. The x-radiation 6 then penetrates a patient 8 under examination.

The x-radiation 6 that has passed through the patient 8 is recorded by an x-ray detector 9 that produces an absorption image of the patient 8, with the structure of the material in the patient 8 that absorbs x-radiation 6 being projected onto the x-ray detector 9. Thus the x-ray recordings that contain absorption images are also known as projection images.

The x-ray detector 9 is preferably a semiconductor-based flat image detector or area detector having a plurality of detector elements with which a digital x-ray image can be produced.

Connected downstream of the x-ray detector 9 is an evaluation unit 10 which linearly combines the absorption images recorded through varying the tube voltage $U_R$ in different energy ranges of the x-radiation 6. The combined image produced by the linear combination of absorption images recorded in different energy ranges is displayed on a display unit 11.

The linear combination of absorption images can entail, for example, forming a difference through which the bone structure of the patient 8 is eliminated from the combined image. The combined image produced in this way contains the absorption structure of the soft tissue, which is advantageous particularly in the case of pulmonary examinations.

The tube voltage $U_R$ and the preliminary filters 7 in particular are varied when performing absorption images in different energy ranges. A lower tube voltage $U_R$ can be used for the absorption image in the low-energy range for example. The preliminary filters 7 can furthermore exhibit a small material thickness so that the low-energy component of the spectrum produced by the x-ray tube 2 will be only negligibly suppressed. Conversely, a high tube voltage $U_R$ can be used for the absorption images in the high-energy range. Preliminary filters 7 having a large material thickness can furthermore also be used that allow only the high-energy component of the spectrum produced by the x-ray tube 2 to pass through.

The efficiency of the x-ray tube 2 rises as a rule linearly with the applied tube voltage $U_R$. Moreover, the effective cross-section of the x-ray quanta in terms of their impact on the material decreases as the quantum energy increases. Consequently more x-ray quanta penetrate the patient 8 in the high-energy range than in the low-energy range. With the same exposure times and x-ray currents, the x-ray detector 9 will thus receive a higher detector dosage in the case of an x-ray recording in the high-energy range than in the case of an x-ray recording in the low-energy range. Consequently the tube current $I_R$ must be increased for low-energy recordings. It must be noted in this regard that the tube current $I_R$ can be more readily increased by heating than decreased, because owing to the vacuum in the x-ray tube a heating sequence takes less time than a cooling sequence.

For this reason first a high-energy radiation pulse 12 and then a low-energy radiation pulse 13 is produced. This temporal sequence enables the temporal interval between the high-energy radiation pulse 12 and the low-energy radiation pulse 13 to be minimized, since the tube current $I_R$ for the low-energy radiation pulse 13 can be increased rapidly.

Furthermore the high-energy radiation pulse 12 is set at the end of an assigned x-ray window 14. In this way the low-energy radiation pulse 13 to which an x-ray window 15 is assigned immediately follows the high-energy radiation pulse 12.

In order to avoid artifacts when switching the mode in which the x-ray detector 9 is operated, the x-ray detector 9 is operated in the same mode each time for the high-energy radiation pulse 12 and the low-energy radiation pulse 13. Consequently the x-ray windows 14 and 15 have the same duration. Thus only one offset image is necessary in each case for the offset adjustment of the x-ray recording recorded in the high-energy range and for the offset adjustment of the x-ray recording recorded in the low-energy range. This offset image can be recorded before or after the two x-ray recordings in the high-energy range and low-energy range.

Figure 2:
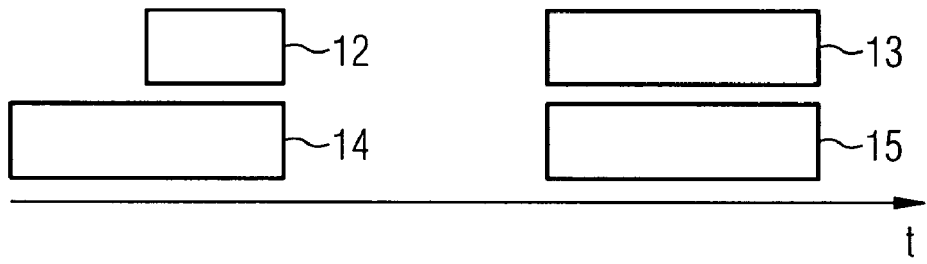
FIG. 2 shows a timing diagram showing the temporal sequence of a high-energy and a low-energy x-ray pulse and the associated x-ray windows.

The advantage of the temporal arrangement of the high-energy radiation pulse 12 shown in FIG. 2 is explained in more detail using the following numerical example: if the duration of each of the x-ray windows 14 and 15 is 80 milliseconds and the read-out time between the two x-ray windows 14 and 15 also amounts to 80 milliseconds, in total 240 milliseconds are needed in order to perform the x-ray recording in the high-energy range and in the low-energy range if the high-energy radiation pulse 12 is performed at the beginning of the assigned x-ray window. By contrast if the high-energy radiation pulse 12 having a duration of 20 milliseconds for example is set at the end of the assigned x-ray window 14, a total time of 180 milliseconds is needed in order to perform the two x-ray recordings. The total time can thus be reduced by 25 percent.

The invention claimed is:

1. A method for recording a projection image of an object under a medical examination, comprising:
   emitting a radiation pulse in a high-energy range by a radiation source to the object at an end of a radiation window of an image detector;
   emitting a radiation pulse in a low-energy range by the radiation source to the object during a further radiation window of the image detector after emitting the radiation pulse in the high-energy range;

recording the projection image of the object by detecting the radiation pulse in the high-energy range and the radiation pulse in the low-energy range via the image detector; and using the projection image in a humanly perceptible manner.

2. The method as claimed in claim 1, wherein the radiation window in the high-energy range and the further radiation window in the low-energy range are respectively assigned to the image detector at the high-energy range and at the low-energy range.

3. The method as claimed in claim 1, wherein the image detector is a digital flat image detector.

4. The method as claimed in claim 1, wherein the radiation pulse in the high-energy range and the radiation pulse in the low-energy range are emitted at a same duration.

5. The method as claimed in claim 1, wherein the radiation pulse in the high-energy range is emitted with a shorter duration than the radiation pulse in the low-energy range.

6. The method as claimed in claim 1, wherein a photon current density of the radiation pulse in the low-energy range is increased.

7. The method as claimed in claim 6, wherein the radiation source is an x-ray tube and the image detector is an x-ray detector.

8. The method as claimed in claim 7, wherein a cathode of the x-ray tube is heated up before emitting the radiation pulse in the low-energy range in order to increase the photon current density.

9. A device for recording a projection image of an object under a medical examination, comprising:

a radiation source that:

emits a radiation pulse in a high-energy range by the radiation source to the object at an end of a radiation window, and emits a radiation pulse in a low-energy range by the radiation source to the object during a further radiation window after the radiation pulse in the high-energy range is emitted; and an image detector that records the projection image of the object by detecting the radiation pulse in the high-energy range and the radiation pulse in the low-energy range.

10. The device as claimed in the claim 9, wherein the radiation window in the high-energy range and the further radiation window in the low-energy range are respectively assigned to the image detector at the high-energy range and the low-energy range.

11. The device as claimed in the claim 9, wherein the image detector is a digital flat image detector.

12. The device as claimed in the claim 9, wherein the radiation pulse in the high-energy range and the radiation pulse in the low-energy range are emitted at a same duration.

13. The device as claimed in the claim 9, wherein the radiation pulse in the high-energy range is emitted with a shorter duration than the radiation pulse in the low-energy range.

14. The device as claimed in the claim 9, wherein a photon current density of the radiation pulse in the low-energy range is increased.

15. The device as claimed in the claim 14, wherein the radiation source is an x-ray tube and the image detector is an x-ray detector.

16. The device as claimed in the claim 15, wherein a cathode of the x-ray tube is heated up before emitting the radiation pulse in the low-energy range in order to increase the photon current density.

* * * * *